United States Patent
Pond

(10) Patent No.: US 6,494,713 B1
(45) Date of Patent: Dec. 17, 2002

(54) NICKEL TITANIUM DENTAL NEEDLE

(76) Inventor: Gary J. Pond, 2816 N. Main St., Racine, WI (US) 53402

( * ) Notice: Subject to any disclaimer, the term of this patent is extended or adjusted under 35 U.S.C. 154(b) by 66 days.

(21) Appl. No.: 09/654,201

(22) Filed: Sep. 1, 2000

Related U.S. Application Data

(63) Continuation-in-part of application No. 09/435,658, filed on Nov. 8, 1999, now abandoned.

(51) Int. Cl.[7] .................................................. A61C 1/00
(52) U.S. Cl. ......................................... 433/81; 433/224
(58) Field of Search ............................ 433/80, 81, 224, 433/91

(56) References Cited

U.S. PATENT DOCUMENTS

| | | | |
|---|---|---|---|
| 1,942,150 A | 1/1934 | Rohn | |
| 3,884,230 A | 5/1975 | Wulff | |
| 4,018,222 A | 4/1977 | McAleer et al. | 206/365 |
| 4,026,025 A | 5/1977 | Hunt | |
| 4,142,531 A | * 3/1979 | Magovern et al. | |
| 4,240,423 A | * 12/1980 | Akhavi | |
| 4,274,555 A | 6/1981 | Sneider | 222/107 |
| 4,431,426 A | 2/1984 | Groshong et al. | 604/280 |
| 4,505,767 A | 3/1985 | Quin | 148/402 |
| 4,512,769 A | 4/1985 | Kozam et al. | 604/209 |
| 4,565,589 A | 1/1986 | Harrison | 148/402 |
| 4,702,260 A | 10/1987 | Wang | 604/264 |
| 4,735,619 A | 4/1988 | Sperry et al. | 604/208 |
| 4,770,725 A | 9/1988 | Simpson et al. | 148/402 |
| 4,979,900 A | * 12/1990 | Okamoto et al. | 433/224 |
| 5,000,912 A | 3/1991 | Bendel et al. | 420/34 |
| 5,127,831 A | 7/1992 | Bab | 433/80 |
| 5,295,978 A | * 3/1994 | Fan et al. | 604/265 |
| 5,378,149 A | * 1/1995 | Stropko | 433/80 |
| 5,533,982 A | 7/1996 | Rizk et al. | 604/232 |
| 5,544,651 A | 8/1996 | Wilk | 604/50 |
| 5,752,825 A | * 5/1998 | Buchanan | 433/32 |
| 5,910,133 A | 6/1999 | Gould | 604/164 |
| 6,012,921 A | 1/2000 | Riitano | 433/102 |
| 6,042,375 A | 3/2000 | Riitano | 433/102 |
| 6,045,362 A | 4/2000 | Riitano | 433/224 |
| 6,059,572 A | 5/2000 | Riitano | 433/224 |
| 6,079,979 A | 6/2000 | Riitano | 433/81 |
| 6,162,202 A | 12/2000 | Sicurelli et al. | 604/272 |

FOREIGN PATENT DOCUMENTS

| | | |
|---|---|---|
| EP | 0 294 210 A1 | 12/1988 |
| EP | 0 440 948 A1 | 8/1991 |
| EP | 0 604 062 A2 | 6/1994 |
| EP | 0 604 062 B1 | 6/1994 |
| EP | 0 440 948 B1 | 8/1995 |
| EP | 0 529 675 B1 | 2/1996 |
| EP | 0 696 213 B1 | 2/1996 |
| JP | 08103456 A | 4/1996 |

OTHER PUBLICATIONS

Article "Parylene Conformal Coatings Specifications and Properties" Date: Nov. 19 1998 Specialty Coating Systems

* cited by examiner

Primary Examiner—Cary E. O'Connor
(74) Attorney, Agent, or Firm—Ryan Kromholz & Manion, S.C.

(57) ABSTRACT

An autoclavable needle assembly and method of making the same is provided for endodontic surgical procedures. The needle assembly includes a supporting hub member containing an adhesive in which one end of the needle is embedded. The surgical needle is preferably fabricated from NiTi alloy and includes, at its distal end, a side vent in the form of a skived portion extending a predetermined distance inwardly from the tip from the distal end of the needle. One or more coatings may be applied to the needle. An angle-adjustment sleeve can be bent to hold a desired angle in the needle.

8 Claims, 7 Drawing Sheets

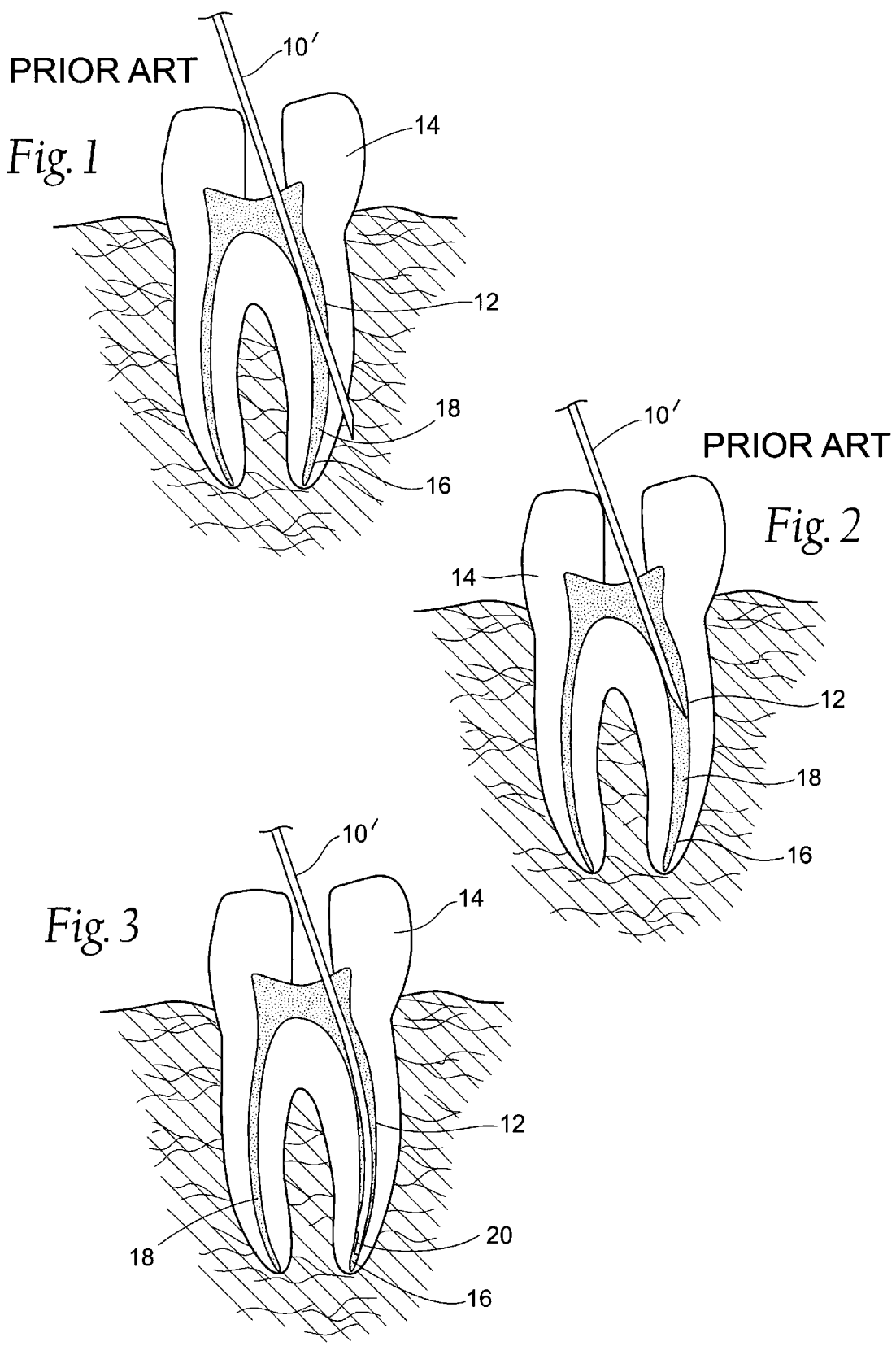

NICKEL TITANIUM DENTAL NEEDLE

This application claims the benefit of and is a continuation-in-part of copending U.S. patent application Ser. No. 09/435,658 filed on Nov. 8, 1999, now abandoned.

BACKGROUND OF THE INVENTION

This invention relates to surgical needles, and in particular, needles used for endodontic procedures, such as root canal surgery. During endodontic procedures, such as root canals, it is necessary to inject or applicate fluid into the dental pulp or root. Presently, typical needles used for these types of procedures are made from relatively inflexible stainless steel. This material has been preferred for its ability to be autoclaved and its relatively inexpensive cost; however, use over time in endodontic applications has revealed several undesirable characteristics. For example, a typical tooth has at least one root. Each root is not straight, but curves toward the centerline of the tooth. The relative rigidity of stainless steel has led to unwanted results when used in root canal surgery due to the needle's inability to bend to the contour of the curved root canal. During a root canal procedure, a dental practitioner drills an opening in a patient's tooth surface enamel and inner dentine to gain access to the dental pulp and surrounding cavity. A hollow, stainless steel surgical needle is inserted into the opening to remove decaying pulp tissue and irrigate the surrounding cavity with sodium hypochlorite solution. The sodium hypochlorite solution rids the canal of bacteria and other foreign substances before sealant is injected into the canal. The dental pulp cavity is curvately elongate and tapers into the root area of the affected tooth. The rigid nature of a stainless steel needle does not allow the flexion necessary to move through the delicately curved root cavity to reach the most distal end. At present, the dental practitioner must exert extreme care in using the stainless steel needle to avoid puncture of the tooth wall and surrounding jaw. Common dental practice at this time is to pre-bend the needle prior to insertion using an X-ray image as a template. Although pre-bending allows the dental practitioner to insert the needle into the root canal somewhat farther than when the needle is left straight, this method is crude at best and full access to the root canal apex cannot be achieved. Should the dental practitioner meet needle resistance during insertion, he must discontinue insertion or risk damage of the tooth and surrounding area. If this occurs, the practitioner must be satisfied with partial depth insertion and subsequent partial irrigation. The tip of the root cannot be accessed so completely so full aspiration and irrigation cannot be accomplished. If the dental practitioner continues insertion after meeting curvature resistance, the risk of punching a hole in the tooth wall becomes great.

The practice of using endodontic surgical needles fabricated from nickel titanium (NiTi) stainless steel is known under the teachings of U.S. Pat. No. 5,000,912 issued to Bendel et al among others, in addition to other nickel titanium alloys disclosed in U.S. Pat. Nos. 4,337,000; 4,565,589; 4,505,767; 4,770,725 and European Patent EP 0 529 675 B1, also granted to Bendel et al. The use of this alloy in connection with conventional endodontic needles has not achieved desired results. The present invention contemplates fabrication of endodontic surgical needles of an alloy of nickel and titanium, per se, including a stainless steel sleeve to allow for manual fixed-angle adjustments in the upper portion of the needle, and a modification of the distal end of the needle to provide a skived, side-vented area.

SUMMARY OF THE INVENTION

It is therefore an object of this invention to provide an autoclavable endodontic needle assembly capable of curving to the configuration of a root canal while being inserted therein. The needle is preferably fabricated from a binary NiTi alloy. The preferred binary NiTi alloy contains 55.8 weight percent Nickel. The needle of the present invention may be produced to be pre-bent to a desired angle; the preferred angle chosen is 45 degrees. The present invention may also include an angle-adjustment sleeve around a portion of the needle to allow for manual adjustment of the pre-bent angle. An adhesive-filled supporting hub member grippingly engages the needle shaft to provide connection to a conventional luer lock. The supporting hub configuration may also be pre-bent to a desired angle, such as 45 degrees, with the protruding needle shaft being straight. The options of straight or pre-angled needle, straight or pre-angled hub portion, and manually adjustable angling sleeve are conceived to give the dental practitioner convenient options for ease of use while working within the awkward confines of a patient's mouth.

Sodium hypochlorite solution, depending upon the solution strength, can be a caustic solution and may have an adverse affect on the preferred binary NiTi alloy. To substantially eliminate the possibility of the solution corroding or deteriorating the NiTi alloy, a coating, such as a parylene polymer, is applied to the needle during its manufacture. While parylene polymers are the preferred coatings, there are other commercially available coatings that provide the same protection. The coating prevents the sodium hypochlorite solution from adversely affecting the physical properties of the dental needle.

It is a further object of the present invention to provide a unique tip for the needle. The tip portion of the present invention includes a skived area at the most distal end of the needle. The skived area allows side venting of irrigation fluid and prevents vacuum build up during aspiration of the root canal. The unique tip is further capable of functioning within the narrow and curved confines of a root canal.

DESCRIPTION OF THE DRAWINGS

FIG. 1 is a longitudinal cross sectional view of a tooth and its normal environment and showing a prior art endodontic needle disposed therein during said procedure.

FIG. 2 is a longitudinal cross sectional view of a tooth and its normal environment and showing a prior art endodontic needle disposed therein during said procedure.

FIG. 3 is a longitudinal cross section the improved needle of the present invention disposed within the tooth cavity.

DETAILED DESCRIPTION

Figure 4:
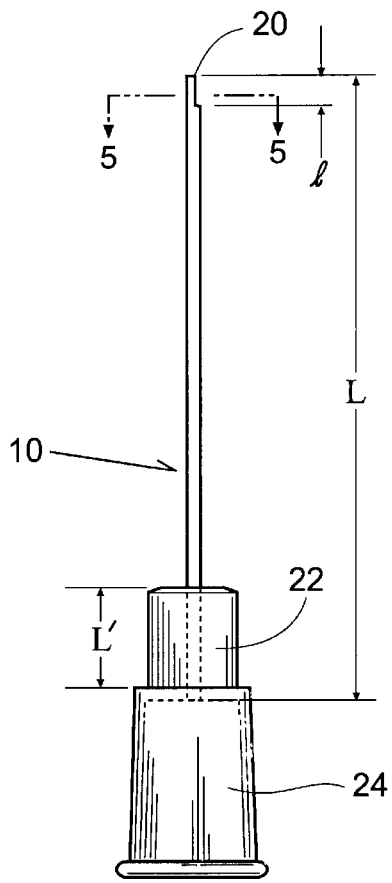
FIG. 4 is an elevational view of the needle and supporting device of the present invention.

Although the disclosure hereof is detailed and exact to enable those skilled in the art to practice the invention, the physical embodiments herein disclosed merely exemplify the invention which may be embodied in other specific structure. While the preferred embodiment has been described, the details may be changed without departing from the invention, which is defined by the claims.

FIGS. 1 and 2 illustrate a prior art dental needle 10' used for endodontic procedures. Needles of this type have been made of relatively rigid stainless steel. This rigidity has created difficulty for the dental practitioner due to their inability to flex and conform to the contours of a typical root canal. As seen in FIG. 1, the prior art needle 10' may puncture the root canal wall 12 if undue pressure is exerted in an attempt to insert the needle 10' farther into a tooth 14 than its capability to flex. FIG. 2 illustrates the prior art needle 10' as inserted to its maximum depth, without puncture of the root canal wall 12; however, the needle 10' is unable to reach the apical constrictive terminus 16 of the root canal 18 of tooth 14. Partial insertion of the needle 10' results in incomplete irrigation and aspiration of the root canal 18 and prevents the complete removal of decay and dental pulp material required in a successful root canal procedure.

Referring to FIG. 3, the needle 10 of the present invention is shown. The needle 10 conforms to the curved contour of the root canal 18 and is thus able to reach the apical constrictive terminus 16 of the root 18 without interruption or diametral confinement. Further, the modified tip 20 allows side venting, thereby reducing undue vacuum and pressure during aspiration and irrigation.

Figure 8:
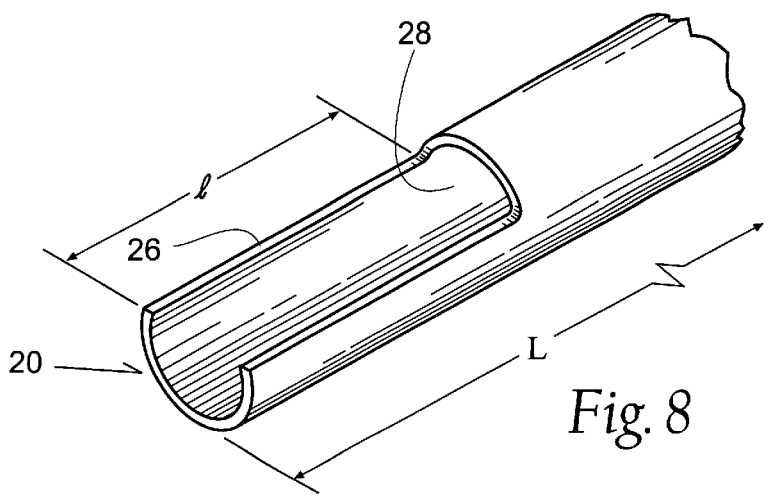
FIG. 8 is a perspective view of the distal end portion of the coated shaft of the surgical needle made according to the present invention.

As seen in FIG. 4, a preferred embodiment of the needle 10 of the present invention is shown. The needle 10 is preferably mounted in a hub member or apparatus 22. The hub apparatus 22 is preferably provided with a cup-like interior and further includes a conventional LUER® connector 24. The connector 24 is also commonly referred to as a slip LUER® or a LUER® lock fitting. The hub apparatus 22 is molded from autoclavable material, such as Ultim 1000, obtainable from General Electric Corporation. The total needle shaft length, (L) may be of any useful length, although the preferred length is 32.26 mm. A portion of the total shaft length (L'), shown in phantom, is it grippingly supported by the hub portion 22. The shaft length (L') is secured to the hub portion 22 with an adhesive (not shown) capable of withstanding autoclavable temperatures as for instance, 135° C. An example adhesive is part number 302-3M, obtained from Epoxy Technology of Billerica, Mass. The length of the supported portion (L') may be of any practical length, but in the present embodiment is preferably 7 mm. The shaft length (L) is further portioned into a distal end skived portion 20 which, in the preferred embodiment is $\frac{1}{25}$ of the needle shaft portion (L) minus the length of the supported portion (L'). In the preferred embodiment (see also FIG. 8), this ratio calculated results in a skived portion length (1) of approximately 1 mm.

Figure 4A:
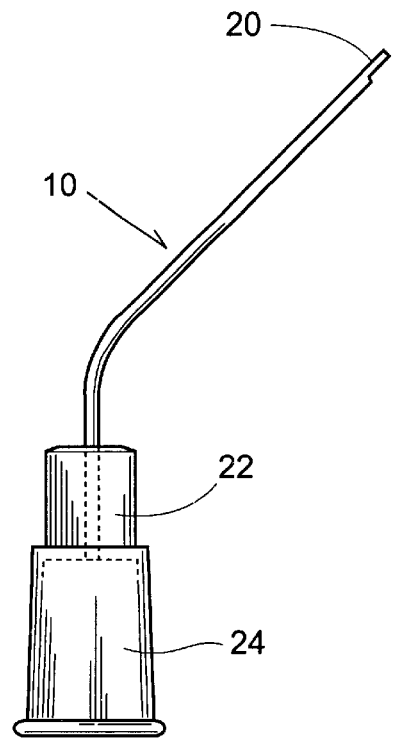
FIG. 4a is an elevational view similar to the view of FIG. 4, and illustrating an alternate needle and supporting device but with the needle being bent to a predetermined angle.

FIG. 4a illustrates an alternate embodiment needle 10 wherein the needle shaft length (L) is pre-bent for ease of use. Although the shaft length (L) could be pre-bent to any convenient angle, the preferred angle is approximately 45 degrees.

Figure 5:
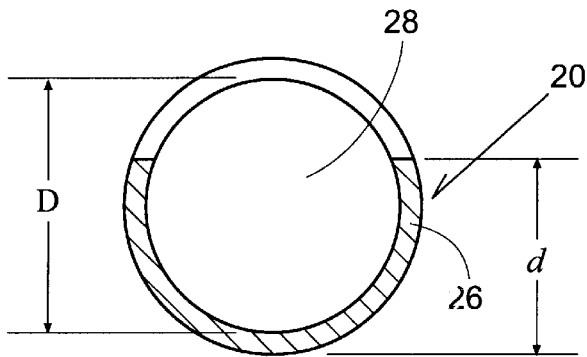
FIG. 5 is a cross sectional view taken along lines 5—5 of FIG. 4.
Figure 7:
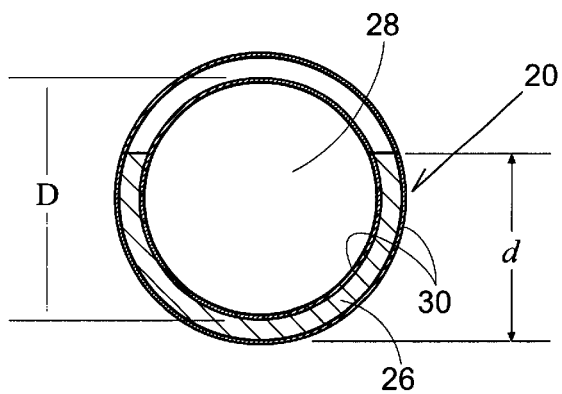
FIG. 7 is a cross sectional view taken along line 7—7 of FIG. 6.

As seen in FIGS. 5 and 7, a cross section of the modified tip 20 shows the skived portion 26 having an arcuate height (d) of approximately $\frac{2}{3}$ the diameter (D) of the needle bore 28. In the preferred embodiment, the diameter (D) of the needle bore 28 is approximately 0.3 mm, although it is to be understood that a greater or lesser bore diameter may also be employed.

Figure 6:
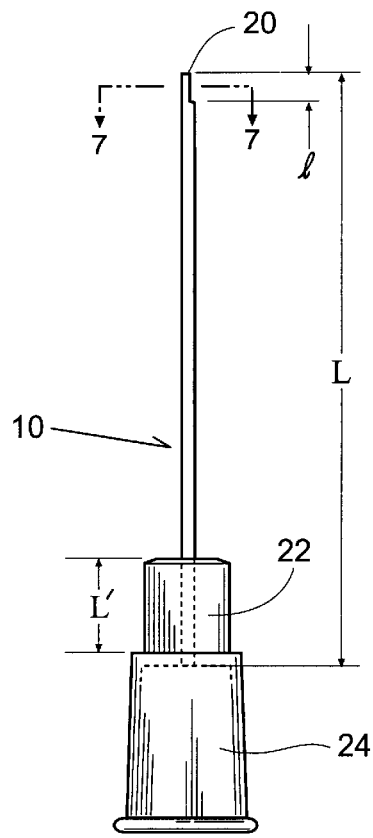
FIG. 6 is an elevational view of the present invention showing a hydrophobic layer coated on the exterior surface of the supported needle.

Another embodiment of the present invention is seen in FIGS. 6 and 7. The needle 10 may be provided with a coating 30 to prevent the possibility of corrosion or deterioration of the needle 10 when exposed to a caustic solution such as sodium hypochlorite. One such acceptable coating 30 is a parylene polymer. Parylene polymers have a very low permeability to moisture and other corrosive gases and fluids. A substantially pin hole free coating can be applied to the exposed metallic surfaces of the NiTi needle 10. It has been found that the coating 30 is most effective in the thickness range of 0.1 to 2.0 microns. Parylenes resist room temperature chemical attack and are insoluble in all organic solvents up to 150 degrees Celsius. The polymer is also resistant to permeation by solvents. The ability to deposit parylene as a truly conformal, thin, continuous uniform adherent coating permits enhances its application to the needle 10.

In addition or in lieu of the polymer coating, the needle 10 may be provided with a hydrophobic lubricant 30 to aid in smooth and fluid insertion into the tooth (not shown in this view). The hydrophobic lubricant 30 also helps prevent residual tissue from re-adhering to itself during aspiration.

Figure 9:
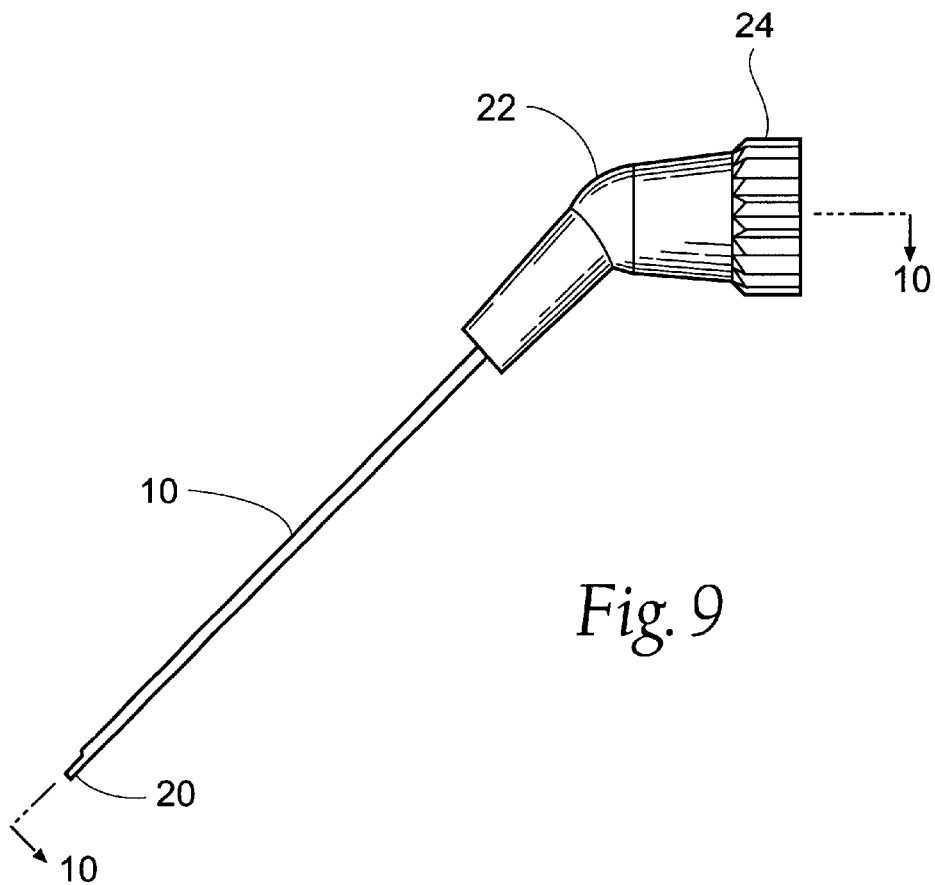
FIG. 9 illustrates a conventional luer connector modified to include a bend intermediate its ends and arranged to receive and secure the surgical needle as shown in preceding figures.
Figure 10:
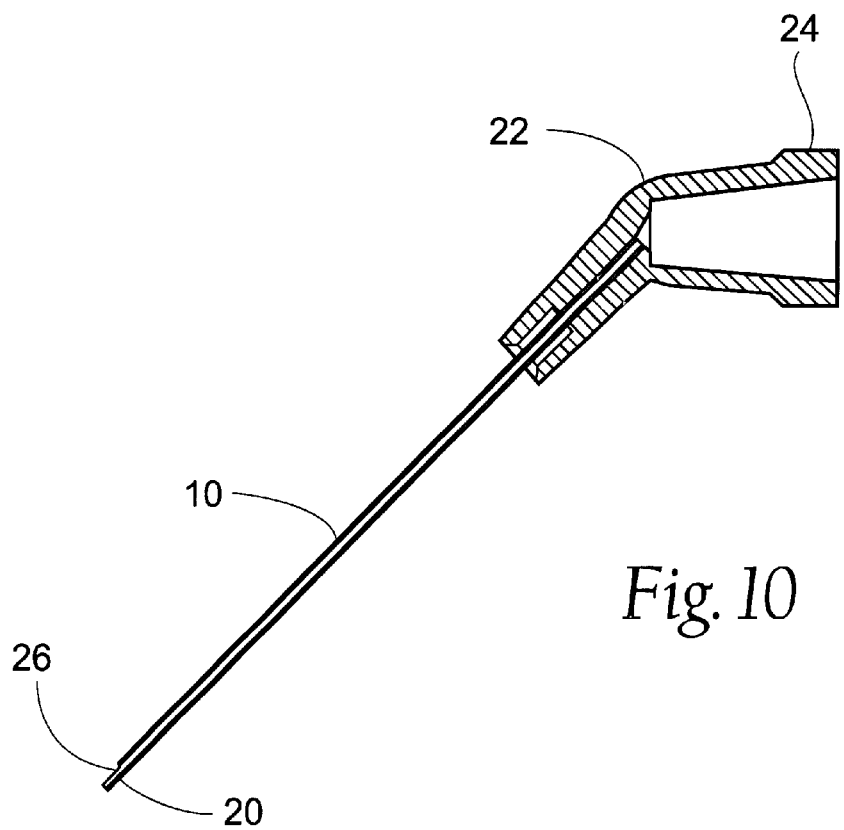
FIG. 10 is a sectional view taken along lines 10—10 of FIG. 9.

With reference to FIGS. 9 and 10, it will be observed that the supporting hub portion 22, itself, may be bent to a predetermined angle, which may be 45°. When the hub portion 22 is bent the needle 10 to be utilized is preferably straight.

Figure 11:
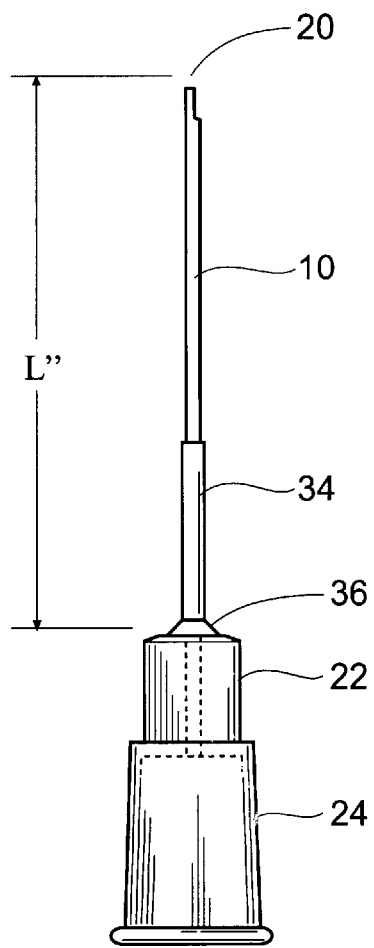
FIG. 11 is an elevational view of the needle, angle-adjustment sleeve and supporting device of the present invention.
Figure 12:
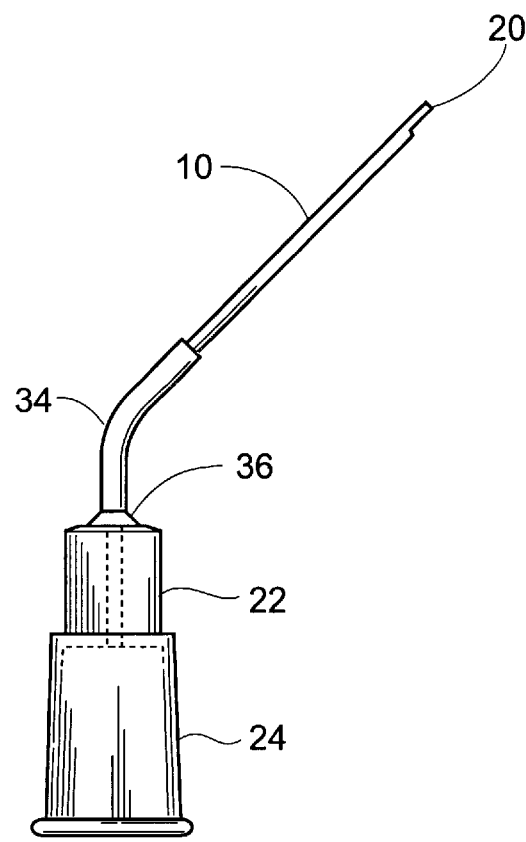
FIG. 12 is an elevational view similar to the view of FIG. 11, and illustrating the angle-adjustment sleeve bent to a desired angle of approximately 45 degrees.
Figure 13:
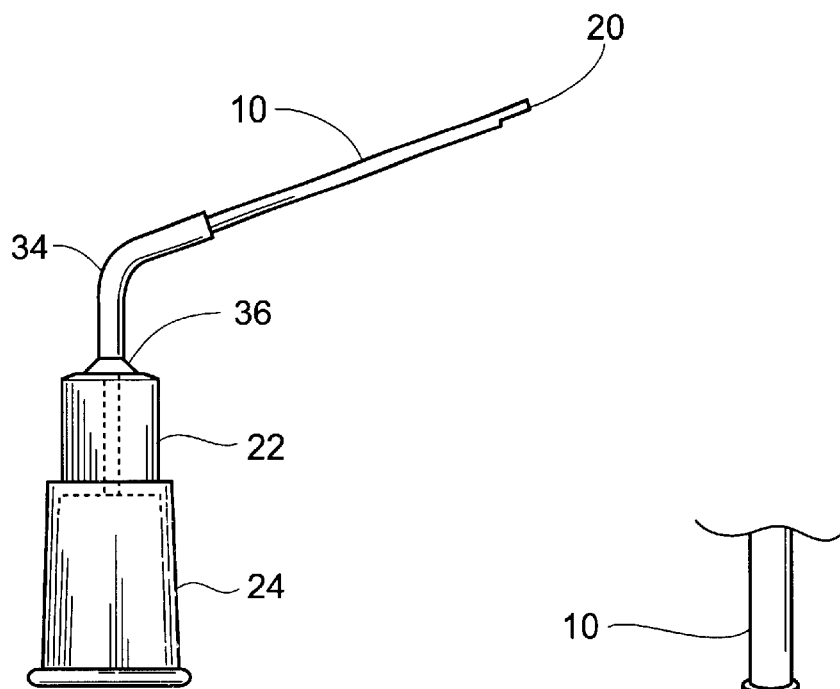
FIG. 13 is an elevational view similar to the view of FIG. 11, and illustrating the angle-adjustment sleeve bent to a desired angle of approximately 70 degrees.

As depicted in FIGS. 11 through 13, inclusive, the present invention may also include an angle-adjustment sleeve 34 for manually pre-bending the needle 10. The adjustment sleeve 34 is preferably made from a fairly rigid material capable of holding the needle 10 at a desired angle, while at the same time being pliable enough to allow for quick adjustment without using tools. It must not kink or bend sharply, but must curve gradually without pinching or compressing the needle 10. The adjustment sleeve 34 may be of any suitable length to hold a desired angle in a desired portion of the needle 10, may be positioned anywhere along the length of the needle 10, and may extend from inside the hub member 22. In the preferred embodiment, the sleeve 34 is made from an annealed stainless steel. It begins just inside the hub member 22 and extends approximately one-third of the exposed length "L" of the needle 10.

Figure 14:
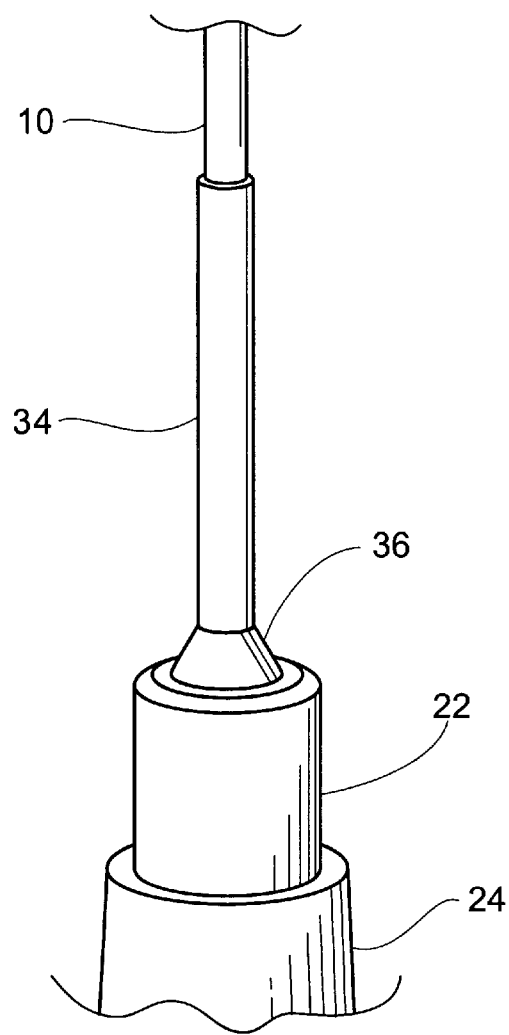
FIG. 14 is a fragmentary perspective view of the present invention, wherein the angle-adjustment sleeve is secured using an adhesive.

The adjustment sleeve 34 may be attached to the needle 10, hub member 22, or both in any conventional fashion. Referring to FIG. 14, a method of securing the sleeve 34 includes using an adhesive 36 capable of withstanding autoclavable temperatures as described above, which may or may not be the same adhesive used to secure the needle 10 to the hub member 22. In the preferred embodiment, the adhesive 36 is used to secure, the sleeve 34 to both the hub member 22 and the needle 10.

Figure 15:
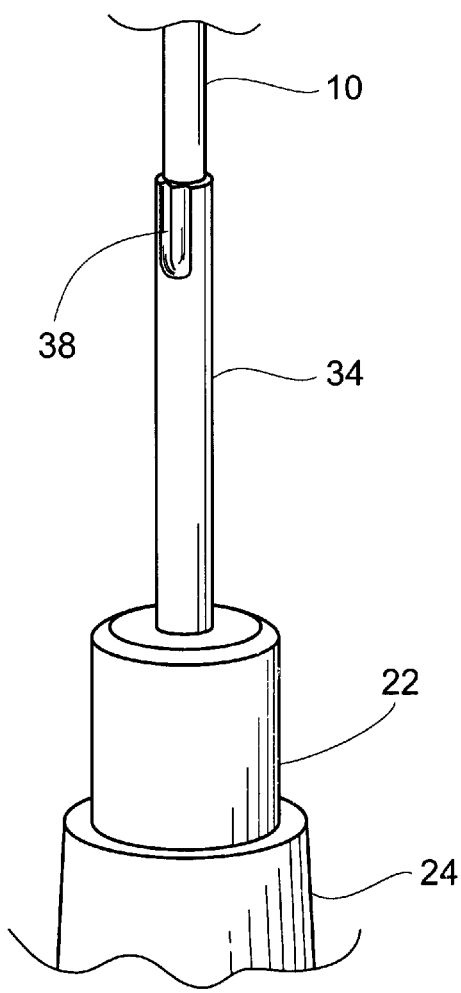
FIG. 15 is a fragmentary perspective view of an alternative embodiment of the present invention, wherein the angle-adjustment sleeve is secured using a pressure stressed connection.
Figure 16:
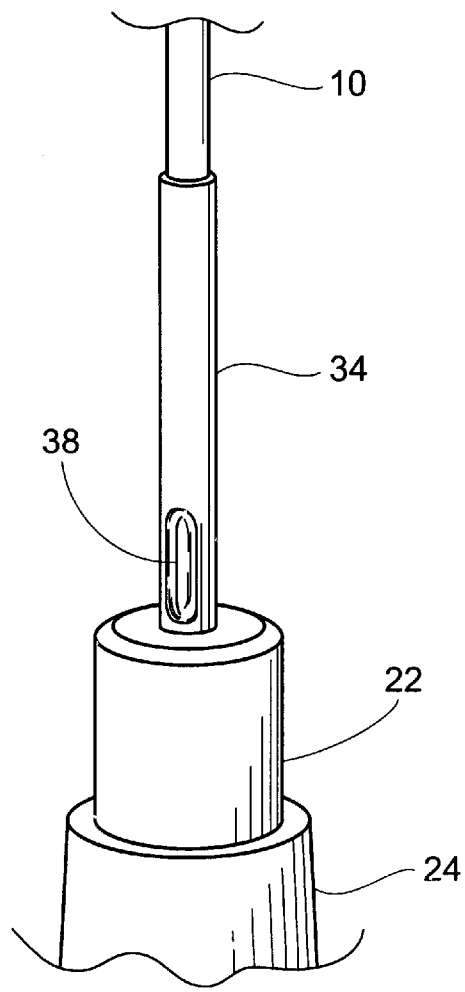
FIG. 16 is a fragmentary perspective view of an alternative embodiment of the present invention, wherein the angle-adjustment sleeve is secured using a pressure stressed connection

Referring to FIGS. 15 and 16, an alternative embodiment of the present invention is depicted, wherein the adjustment sleeve 34 may be secured to the needle with a pressure stressed connection 38. The connection 38 is a deformation in the sleeve 34, such as a crimped or swaged connection, that prevents the sleeve 34 from moving relative to the needle 10. Although the connection 38 secures the sleeve 34 tightly, it does not cause a notable deformation in the needle 10, or prevent dental material from passing through the needle 10. The stressed connection 38 may be made at any location along the length of the sleeve 34, and two included locations are depicted in FIGS. 15 and 16.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

What is claimed is:

1. A surgical needle assembly for endodontic procedures, said assembly comprising:
   a needle having one end encapsulated and grippingly supported by a hub member and including a coextensive bore;
   said needle further including a protruding hollow shaft portion of predetermined length;
   an angle-adjustment sleeve surrounding a portion of said needle;
   the distal end of said needle including an arcuate longitudinal skived portion having an arcuate height of a predetermined proportional ratio relative to the diameter of said bore.

2. The needle assembly of claim 1, wherein the angle-adjustment sleeve is formed from an annealed stainless steel.

3. The needle assembly of claim 1, wherein the angle-adjustment sleeve is secured to said hub member.

4. The needle assembly of claim 1, wherein the angle-adjustment sleeve is adhesively secured to said hub member.

5. The needle assembly of claim 1, wherein the angle-adjustment sleeve is secured to said needle using a pressure stressed connection.

6. The needle assembly of claim 1, wherein the angle-adjustment sleeve surrounds approximately one-third of the needle protruding hollow shaft portion.

7. A method of fabricating a surgical needle assembly for endodontic procedures including the steps of:
   providing a tubular shaft;
   die cutting said shaft to provide a surgical needle of predetermined length;
   machining one end of said needle to provide a skived portion of predetermined length;
   providing a hub member having a cup-like interior;
   supplying an autoclavable adhesive to the cup-like interior of said hub member; and
   inserting the opposite end in said adhesive for retention and support thereof by said hub member;
   providing an angle-adjustment sleeve;
   placing said angle-adjustment sleeve over the needle and into said adhesive for retention and support thereof by said hub member.

8. A method of fabricating a surgical needle assembly for endodontic procedures including the steps of:
   providing a tubular shaft;
   die cutting said shaft to provide a surgical needle of predetermined length;
   machining one end of said needle to provide a skived portion of predetermined length;
   providing a hub member having a cup-like interior;
   supplying an autoclavable adhesive to the cup-like interior-of said hub member; and
   inserting the opposite end in said adhesive for retention and support thereof by said hub member;
   providing an angle-adjustment sleeve;
   positioning said angle-adjustment sleeve over said needle;
   forming a pressure stressed connection between said angle-adjustment and said needle by deforming said angle-adjustment sleeve.

* * * * *

UNITED STATES PATENT AND TRADEMARK OFFICE
CERTIFICATE OF CORRECTION

PATENT NO.    : 6,494,713 B1
DATED         : December 17, 2002
INVENTOR(S)   : Gary J. Pond It is certified that error appears in the above-identified patent and that said Letters Patent is hereby corrected as shown below:

<u>Title page, Item [54] and Column 1, line 1,</u>
Title should read:
-- SURGICAL NEEDLE --

Signed and Sealed this

Twenty-ninth Day of April, 2003

JAMES E. ROGAN
*Director of the United States Patent and Trademark Office*